United States Patent [19]
Yamada et al.

[11] Patent Number: 5,693,374
[45] Date of Patent: Dec. 2, 1997

[54] ALPHA-RESORCYCLIC ACID ESTER DERIVATIVES AND RECORDING MATERIALS USING THE SAME

[75] Inventors: Hisao Yamada; Shunsaku Higashi; Ken Iwakura, all of Shizuoka, Japan

[73] Assignee: Fuji Photo Film Co., Ltd., Kanagawa, Japan

[21] Appl. No.: 492,795

[22] Filed: Jun. 20, 1995

[30] Foreign Application Priority Data

Jun. 23, 1994 [JP] Japan .................. 6-141477

[51] Int. Cl.$^6$ .................. C08J 7/18; C07C 69/88
[52] U.S. Cl. .................. 427/506; 346/150.3; 560/70
[58] Field of Search .................. 560/70; 427/806; 346/150.3

[56] References Cited

U.S. PATENT DOCUMENTS 4,446,209  5/1984  Iwakura et al. .................. 346/216

Primary Examiner—Paul J. Killos
Attorney, Agent, or Firm—Sughrue,Mion,Zinn,Macpeak & Seas, PLLC

[57] ABSTRACT

α-resorcylic acid ester derivatives useful as electron-accepting compounds for recording materials, and highly durable recording materials containing these derivatives. The α-resorcylic acid derivative is represented by the following general formula (I),

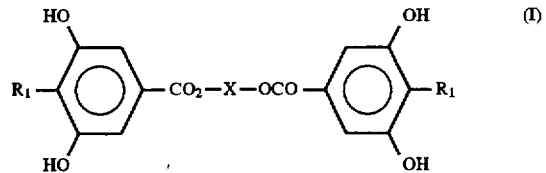

wherein $R_1$ represents a hydrogen atom, a halogen atom or an alkyl group, and X represents a divalent group.

9 Claims, No Drawings

ALPHA-RESORCYCLIC ACID ESTER DERIVATIVES AND RECORDING MATERIALS USING THE SAME

FIELD OF THE INVENTION

The present invention relates to α-resorcylic acid ester derivatives useful as electron-accepting compounds for recording materials. The present invention also relates to recording materials containing such derivatives to provide excellent color developability and high storage stability in the image area.

BACKGROUND OF THE INVENTION

Recording materials comprising an electron-donating colorless dye and an electron-accepting compound are well known. These recording materials serve as pressure-sensitive paper, heat-sensitive paper, photo- and pressure-sensitive paper, electrothermo-recording paper and heat-sensitive transfer paper. Details of such recording materials can be found, for example, in British Patent 2,140,449, U.S. Pat. Nos. 4,480,052 and 4,436,920, JP-B-60-23992 (the term "JP-B" as used herein means an "examined Japanese Patent Publication"), JP-A-57-179836 (the term "JP-A" as used herein means an "unexamined published Japanese patent application"), JP-A-60-123556 and JP-A-60-123557.

Recently, extensive studies have been carried out to improve the characteristics of a recording material, including (1) developed color density and color development sensitivity and (2) storage stability in each of the non-image area and image areas. Known electron-accepting compounds for combination with electron-donating compounds include various compounds such as bisphenol A, p-hydroxybenzoates, bis-(4-hydroxyphenyl)sulfones, etc. Each of these compounds, however, have some drawbacks with respect to developed color density, color development sensitivity, storage stability in the non-image and image areas (light resistance, heat resistance, chemical resistance, plasticizer resistance), etc. For example, bisphenol A used in a heat-sensitive recording material has a problem in that colors fade or disappear in the image area upon storage in the dark under high temperatures.

SUMMARY OF THE INVENTION

The present invention provides an electron-accepting compound for recording materials which have excellent color-developing properties and excellent storage stability in the image area, and furthermore provides a recording material containing the electron-accepting compound.

The above described problems of the prior art are solved by providing a recording material comprising a support having thereon a heat-sensitive recording layer comprising a binder, an electron-donating colorless dye and an electron-accepting compound, wherein the electron-accepting compound is an α-resorcylic acid ester derivative represented by the following general formula (I):

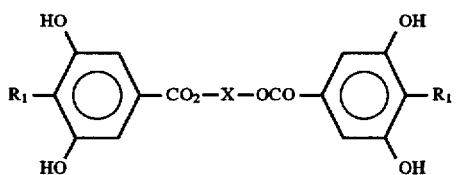

In the above formula, $R_1$ represents a hydrogen atom, a halogen atom or an alkyl group, and X represents a divalent group.

The group represented by $R_1$ in general formula (I) is preferably a hydrogen atom or an alkyl group containing 1 to 4 carbon atoms.

The divalent group represented by X in general formula (I) is preferably an alkylene group containing 1 to 20 carbon atoms, an aralkylene group containing 8 to 20 carbon atoms, an alkenylene group containing 4 to 18 carbon atoms, an alkynylene group containing 4 to 18 carbon atoms or an arylene group containing 6 to 12 carbon atoms. The alkylene group represented by X may contain oxygen or sulfur atom(s) in its molecular chain. Furthermore, the divalent group represented by X may be substituted by one or more substituent groups. Examples of the substituent groups include an alkyl group containing 1 to 12 carbon atoms, an alkoxy group containing 1 to 12 carbon atoms, an aryloxy group containing 6 to 20 carbon atoms and a halogen atom.

DETAILED DESCRIPTION OF THE INVENTION

The divalent group represented by X is preferably an unsubstituted alkylene group containing 2 to 12 carbon atoms, an aralkylene group containing 8 to 12 carbon atoms, an unsubstituted alkenylene group containing 4 to 10 carbon atoms, or an alkylene group containing 5 to 12 carbon atoms and having oxygen atom(s) in its molecular chain.

Specific examples of the compound represented by general formula (I) are given below, but the present invention should not be construed as being limited to these examples.

Specifically, the examples include
bis(3,5-dihydroxyphenylcarboxy)methane,
1,2-bis(3,5-dihydroxyphenylcarboxy)ethane,
1,3-bis(3,5-dihydroxyphenylcarboxy)propane,
1,4-bis(3,5-dihydroxyphenylcarboxy)butane,
1,5-bis(3,5-dihydroxyphenylcarboxy)pentane,
1,6-bis(3,5-dihydroxyphenylcarboxy)hexane,
1,7-bis(3,5-dihydroxyphenylcarboxy)heptane,
1,8-bis(3,5-dihydroxyphenylcarboxy)octane,
1,9-bis(3,5-dihydroxyphenylcarboxy)nonane,
1,10-bis(3,5-dihydroxyphenylcarboxy)decane,
1,11-bis(3,5-dihydroxyphenylcarboxy)undecane,
1,12-bis(3,5-dihydroxyphenylcarboxy)dodecane,
1,15-bis(3,5-dihydroxyphenylcarboxy)pentadecane,
1,2-bis(3,5-dihydroxyphenylcarboxy)propane,
1,3-bis(3,5-dihydroxyphenylcarboxy)-2,2-dimethylpropane,
1,4-bis(3,5-dihydroxyphenylcarboxy)pentane,
1,5-bis(3,5-dihydroxy-4-methylphenylcarboxy)pentane,
1,5-bis(3,5-dihydroxy-4-ethylphenylcarboxy)pentane,
1,5-his(3,5-dihydroxy-4-fluorophenylcarboxy)pentane,
1,5-bis(3,5-dihydroxy-4-chlorophenylcarboxy)pentane,
1,5-bis(3,5-dihydroxy-4-bromophenylcarboxy)pentane,
1,4-bis(3,5-dihydroxyphenylcarboxy)cyclohexane,
1,3-bis(3,5-dihydroxyphenylcarboxy)cyclohexane,
1,2-bis(3,5-dihydroxyphenylcarboxy)cyclohexane,
1,4-bis[(3,5-dihydroxyphenylcarboxy)methyl]benzene,
1,4-bis[(3,5-dihydroxyphenylcarboxy)methyl]-2,3,5,6-tetramethylbenzene,
1,3-bis[(3,5-dihydroxyphenylcarboxy)methyl]benzene,
1,2-bis[(3,5-dihydroxyphenylcarboxy)methyl]benzene,
1,5-bis(3,5-dihydroxyphenylcarboxy)-3-oxapentane,
1,4-bis(3,5-dihydroxyphenylcarboxy)butane-2-ene,
1,4-bis(3,5-dihydroxyphenylcarboxy)butane-2-ine,
1,8-bis(3,5-dihydroxyphenylcarboxy)-3,6-dioxaoctane,
1,4-bis[(3,5-dihydroxy-4-methylphenylcarboxy)methyl]benzene,
1,4-bis[(3,5-dihydroxyphenylcarboxy)methyl]cyclohexane,
1,4-bis(3,5-dihydroxyphenylcarboxyethoxy)benzene, 1,3-bis(3,5-dihydroxyphenylcarboxyethoxy)benzene,
1,2-bis(3,5-dihydroxyphenylcarboxyethoxy)benzene,
4,4'-bis(3,5-dihydroxyphenylcarboxyethoxyphenyl)sulfone,
2,2-bis(3,5-dihydroxyphenylcarboxyethoxyphenyl)propane,
1,4-bis(3,5-dihydroxyphenylcarboxyethoxycumyl)benzene,
4,4'-bis(3,5-dihydroxyphenylcarboxyethoxy)biphenyl,
2,2'-bis(3,5-dihydroxyphenylcarboxyethoxy)biphenyl,
4,4'-bis(3,5-dihydroxyphenylcarboxyethoxyphenyl)sulfide,
4,4'-bis(3,5-dihydroxyphenylcarboxyethoxydiphenyl)ether,
etc.

The α-resorcylic acid ester derivatives of the present invention represented by general formula (I) are readily obtained by reacting the corresponding α-resorcylic acids with dihalide compounds or disulfonate compounds in the presence of a deacidifying agent, or by reacting the corresponding α-resorcylic acids or the lower esters thereof with diol compounds in the presence of a catalyst.

Examples of the electron-donating colorless dyes for use in the present invention include various known compounds such as triphenylmethane phthalide compounds, fluoran compounds, phenothiazine compounds, indolyl phthalide compounds, leucoauramine compounds, rhodamine lactam compounds, triphenylmethane compounds, triazene compounds, spiropyran compounds, fluorene compounds, etc. Specific examples of phthalides are described, e.g., in U.S. Reissued Pat. No. 23024, and U.S. Pat. Nos. 3,491,111, 3,491,112, 3,491,116 and 3,509,174; specific examples of fluorans are described, e.g., in U.S. Pat. Nos. 3,624,107, 3,627,787, 3,641,011, 3,462,828, 3,681,390, 3,920,510 and 3,959,571; specific examples of spirodipyrans are described, e.g., in U.S. Pat. No. 3,971,808; specific examples of pyridine or pyrazine compounds are described, e.g., in U.S. Pat. Nos. 3,775,424, 3,853,869 and 4,264,318; and specific examples of fluorene compounds are described, e.g., in JP-A-59-199757 and JP-A-63-41183.

The α-resorcylic acid ester derivatives of the present invention can be used together with conventional electron-accepting compounds such as phenol derivatives, salicylic acid derivatives, the metal salts of aromatic carboxylic acids, acid clay, bentonite, novolak resins, metal-treated novolak resins, metal complexes and the like. Specific examples of such compounds are described, e.g., in JP-B-40-9309, JP-B-45-14039, JP-A-56-140483, JP-A-48-51510, JP-A-57-210886, JP-A-58-87089, JP-A-59-11286, JP-A-60-76795 and JP-A-61-95988. When used together with other electron-accepting compounds, the α-resorcylic acid ester derivatives of the present invention are preferably used in a proportion of at least 50% by weight to the entire content of the electron-accepting compounds.

A recording material of the present invention when used for a heat sensitive paper may have the structure described in JP-B-59-53193, JP-A-59-197463 or JP-A-62-114989. Specifically, the recording material contains the electron-donating colorless dye and the electron-accepting compound in the form of ground grains measuring no greater than 10 μm, preferably no greater than 3 μm, in size and dispersed in a dispersing medium binder. A 0.5 to 10% water solution of water-soluble high molecular compound is generally used as the dispersing medium. Suitable examples of the water-soluble molecular compound include polyvinyl alcohol, hydroxyethyl cellulose, hydroxypropyl cellulose, epichlorohydrin-modified polyamides, an ethylene-maleic anhydride copolymer, a styrene-maleic anhydride copolymer, an isobutylene-maleinsalicylic acid anhydride copolymer, polyacrylic acid, polyacrylic acid amide, methylol-modified polyacrylamide, starch derivatives, casein, gelatin and the like. For the purpose of imparting water-resistance to the above described dispersing medium binder, a water resistance agent or an emulsion of a hydrophobic polymer, such as a styrene-butadiene rubber latex or an acrylic resin emulsion may be added thereto.

In a light- and heat-sensitive recording material which has on a support a recording layer containing a diazo compound, a coupling component and an organic base and a recording layer containing an electron-donating colorless dye and an electron-accepting compound, the α-resorcylic acid ester derivatives of the present invention can be used as the electron-accepting compound. The light- and heat-sensitive recording materials of the aforementioned type are described, e.g., in JP-A-4-135787, JP-A-4-144784, JP-A-4-144785, JP-A-4-194842, JP-A-4-247447, JP-A-4-247448, JP-A-4-340540, JP-A-4-340541 and JP-A-5-34860.

The dispersion is carried out using a ball mill, a sand mill, a horizontal type sand mill, an attrition mill, a colloidal mill and the like.

In the recording layer, the ratio of the electron-donating colorless dye to the α-resorcylic acid derivative is preferably in the range of from 1:10 to 1:1, particularly preferably from 1:5 to 2:3, by weight.

For the purpose of improving heat responsiveness, a heat fusible material can be incorporated into the heat-sensitive recording layer. Representative examples of the heat fusible material include aromatic ethers, thioethers, esters and/or aliphatic amides or ureides. Specific examples of the heat-fusible material are described, e.g., in JP-A-58-57989, JP-A-58-87094, JP-A-61-58789, JP-A-62-109681, JP-A-62-132674, JP-A-63-151478 and JP-A-63-235961.

The heat-fusible material alone may be dispersed, or the heat-fusible material may be finely dispersed together with the electron-donating colorless dye or the α-resorcylic acid ester derivative. The heat-fusible material is added in a proportion ranging from 20 to 300% by weight, particularly from 40 to 150% by weight, to the α-resorcylic acid ester derivatives.

To the dispersion thus obtained, additives are optionally added as needed. Examples of the additives include an oil-absorbing material, such as an inorganic pigment, a polyurea filler, etc. for preventing staining of a recording head during recording, and a surface lubricant, such as a fatty acid, a metal soap, etc., for improving releasability from the head. In addition to the electron-donating colorless dye and the electron-accepting compound, therefore, various additives, including a heat-fusible material, a pigment, a wax, an antistatic agent, a UV absorbent, an antifoaming agent, a conductive agent, a fluorescent dye and a surfactant, are generally admixed together to prepare a heat-sensitive coating composition. The heat-sensitive coating composition thus prepared is applied to a support such as wood free paper, a wood free paper provided with a subbing layer, a synthetic paper, a plastic film or the like. For good dot reproducibility, the support preferably has a smoothness of at least 500 seconds, particularly at least 800 seconds, as defined by JIS-8119.

Furthermore, a protective layer may be provided on the surface of the heat-sensitive recording layer, as needed. The protective layer may optionally comprise two or more layers. In addition, a coating composition similar to that for the protective layer may be applied to the back side of the support for correcting the curl balance of the support or heightening the chemical resistance of the back side. On the other hand, an adhesive may be applied to the back side of a support and further combined with a release paper, to thereby form a label.

The electron-donating colorless dye for use in the present invention is not particularly limited as to its coverage on a support, but the coverage is preferably in the range of from 0.1 to 2.0 g/m², particularly from 0.2 to 1.5 g/m². The coverage of the α-resorcylic acid ester derivatives on a support is preferably in the range of from 0.1 to 2.0 g/m².

The subbing layer provided on the support preferably contains a pigment as a main component. Organic and inorganic pigments can generally be used as the pigment. In particular, those having an oil absorption of at least 40 cc/100 g when determined according to JIS-K5101 are advantageous. Specific examples of the pigment include calcium carbonate, barium sulfate, titanium oxide, talc, agalmatolite, kaoline, calcined kaoline, aluminum hydroxide, noncrystalline silica, urea-formaldehyde resin powder, polyethylene resin powder and the like. The coverage of the pigment on the support is preferably at least 2 g/m², and more preferably at least 4 g/m².

Water-soluble high molecular compounds or water-soluble binders may be used alone or as a mixture of two or more thereof as the binder for the subbing layer.

Specific examples of the water-soluble high molecular compound include methyl cellulose, carboxymethyl cellulose, hydroxymethyl cellulose, starches,. gelatin, gum arabic, casein, hydrolysis products of a styrene-maleic anhydride copolymer, hydrolysis products of an ethylene-maleic anhydride copolymer, polyvinyl alcohol and polyacrylamide, etc.

Examples of water-soluble binders generally include a synthetic rubber latex or a synthetic resin emulsion. Specific examples thereof include a styrene-butadiene rubber latex, an acrylonitrile-butadiene rubber latex, a methylacrylate-butadiene rubber latex and a vinyl acetate emulsion.

The proportion of binder to pigment ranges from 3 to 100% by weight, preferably from 5 to 50% by weight. Wax, an agent for inhibiting color fading, a surfactant and the like may be added to the subbing layer as needed.

Examples of pigments that may be added to the recording layer include kaoline, calcined kaoline, talc, agalmatolite, diatomaceous earth, calcium carbonate, aluminum hydroxide, magnesium hydroxide, zinc oxide, lithopone, noncrystalline silica, colloidal silica, calcined gypsum, silica, magnesium carbonate, titanium oxide, alumina, barium carbonate, barium sulfate, mica, microballoon, urea-formaldehyde filler, polyester particles, cellulose filler and the like.

Examples of the metal soap include polyvalent metal salts of higher fatty acids, such as zinc stearate, aluminum stearate, calcium stearate, zinc oleate and the like.

Wax having a melting point of from 40° C. to 120° C. may also be added to the recording layer of the present invention for matching properties to a head installed in a facsimile machine. Suitable examples of the wax include paraffin wax, polyethylene wax, carnauba wax, microcrystalline wax, candelilla wax, montan wax and fatty acid amide wax. In particular, paraffin wax, montan wax and methylol stearoamide, each of which have melting points in the range of 50° C. to 100° C., are preferred. The wax is used in a proportion of from 5 to 200% by weight, preferably from 20 to 150% by weight, to the electron-donating colorless dye.

For improving stability to light, a UV absorbent may be added. Examples of the UV absorbent include cinnamic acid derivatives, benzophenone derivatives, benzotriazolylphenol derivatives and the like. More specifically, butyl α-cyano-β-phenyl cinnamate, o-benzotriazolephenol, o-benzotriazole-p-chlorophenol, o-benzotriazole-2,4-di-t-butylphenol, o-benzotriazolyl-2,4-di-t-octylphenol and the like are examples of the foregoing derivatives. As for the hindered phenol compounds, phenol derivatives substituted with a branched alkyl group in at least one of the 2- or 6-position are preferred.

Examples of the water resistance agent include water-soluble initial condensates such as N-methylolurea, N-methylolmelamine, urea-formaldehyde, etc.; dialdehyde compounds such as glyoxal, glutaraldehyde, etc.; inorganic cross-linking agents such as boric acid, borax, etc.; and heat-treated products of a blend such as polyacrylic acid/a methylvinyl ether-maleic acid copolymer/an isobutylene-maleic anhydride copolymer, etc.

Suitable examples of materials used in the protective layer include water-soluble polymers, such as polyvinyl alcohol, carboxy-modified polyvinyl alcohols, a vinyl acetate-acrylamide copolymer, silicon-modified polyvinyl alcohols, starch, denatured starches, methyl cellulose, carboxymethyl cellulose, hydroxymethyl cellulose, gelatins, gum arabic, casein, the hydrolysis products of a styrene-maleic acid copolymer, the hydrolysis products of a styrene-maleic acid half ester copolymer, the hydrolysis products of an isobutylene-maleic anhydride copolymer, polyacrylamide derivatives, polyvinylpyrrolidone, sodium polystyrenesulfonate, sodium alginate, etc., and water-insoluble polymers, such as a styrene-butadiene rubber latex, an acrylonitrile-butadiene rubber latex, a methylacrylate-butadiene rubber latex, an vinyl acetate emulsion, etc.

To the protective layer, pigments, metal soap, wax, a water resistance agent and the like may be added to improve the matching properties to a thermal head. In coating the protective layer on the heat sensitive color-development layer, a surfactant may be added to the protective layer in order to render the protective layer uniform. Examples of the surfactant include alkali metal salts of sulfosuccinic acid derivatives and fluorine-containing surfactants. More specifically, sodium or ammonium salts of di-(n-hexyl) sulfosuccinic acid, di-(2-ethylhexyl)sulfosuccinic acid and the like are preferably used. However, anionic surfactants generally may produce the intended effect. Also, an ultraviolet absorbent may be added to the protective layer for improving stability to light.

Examples of the present invention are shown below, but the invention should not be construed as being limited to these Examples. Additionally, all percentages and all parts in the following Examples are by weight unless otherwise indicated.

EXAMPLE 1

Synthesis of 1,5-Bis(3,5-dihydroxyphenylcarboxy) pentane [$R_1$=H and X=—($CH_2$)$_5$— in general formula (I)]

(Synthesis Example 1)

To a 200 ml solution containing 10.0 g (186 millimole) of sodium methoxide in dimethyl acetamide were added 30.0 g (195 millimole) of α-resorcylic acid and 19.5 g (85 millimole) of 1,5-dibromopentane. The resulting solution was stirred at 100° C. for 3 hours. The reaction mixture obtained was poured into ice-cold water, made acidic by the addition of hydrochloric acid, and then extracted with ethyl acetate. The organic phase was successively washed with an aqueous solution of sodium hydrogen carbonate and saturated brine, and dried over magnesium sulfate. After the solvent was distilled away, the residue was purified by column chromatography. Thus, 27.4 g (yield: 86%) of 1,5-bis(3,5-dihydroxyphenylcarboxy)pentane was obtained. The melting point (abbreviated as m.p. hereinafter) of the product was 184°–186° C.

(Synthesis Example 2)

To a catalytic amount of a toluene solution of p-toluenesulfonic acid were added 16.8 g (100 millimole) of α-resorcylic acid methyl ester and 5.15 g (50 millimole) of 1,5-dihydroxypentane. The resulting mixture was stirred for 6 hours under reflux. The reaction mixture obtained was poured into ice-cold water, and extracted with ethyl acetate. The organic phase was successively washed with an aqueous solution of sodium hydrogen carbonate and saturated brine, and dried over magnesium sulfate. After the solvent was distilled away, the residue was purified by column chromatography. Thus, 13.0 g (yield: 60%) of 1,5-bis(3,5-dihydroxyphenylcarboxy)pentane was obtained.

EXAMPLE 2

Synthesis of Bis(3,5-dihydroxyphenylcarboxy) methane

The same reaction as in Example 1 was carried out, except that 1,5-dibromopentane used in Synthesis Example 1 was replaced by the same mole of dibromomethane, to thereby obtain the intended compound. m.p. 258°–260° C.

EXAMPLE 3

Synthesis of 1,2-Bis(3,5-dihydroxyphenylcarboxy) ethane

The same reaction as in Example 1 was carried out, except that 1,5-dibromopentane used in Synthesis Example 1 was replaced by the same mole of 1,2-dibromoethane, to thereby obtain the intended compound. m.p. 213°–217° C.

EXAMPLE 4

Synthesis of 1,3-Bis(3,5-dihydroxyphenylcarboxy) propane

The same reaction as in Example 1 was carried out, except that 1,5-dibromopentane used in Synthesis Example 1 was replaced by the same mole of 1,3-dibromopropane, to thereby obtain the intended compound. m.p. 205°–208° C.

EXAMPLE 5

Synthesis of 1,4-Bis(3,5-dihydroxyphenylcarboxy) butane

The same reaction as in Example 1 was carried out, except that 1,5-dibromopentane used in Synthesis Example 1 was replaced by the same mole of 1,4-dibromobutane, to thereby obtain the intended compound. m.p. 251°–255° C.

EXAMPLE 6

Synthesis of 1,6-Bis(3,5-dihydroxyphenylcarboxy) hexane

The same reaction as in Example 1 was carried out, except that 1,5-dibromopentane used in Synthesis Example 1 was replaced by the same mole of 1,6-dibromohexane, to thereby obtain the intended compound. m.p. 185°–188° C.

EXAMPLE 7

Synthesis of 1,8-Bis(3,5-dihydroxyphenylcarboxy) octane

The same reaction as in Example 1 was carried out, except that 1,5-dibromopentane used in Synthesis Example 1 was replaced by the same mole of 1,8-dibromooctane, to thereby obtain the intended compound. m.p. 170°–175° C.

EXAMPLE 8

Synthesis of 1,10-Bis(3,5-dihydroxyphenylcarboxy) decane

The same reaction as in Example 1 was carried out, except that 1,5-dibromopentane used in Synthesis Example 1 was replaced by the same mole of 1,10-dibromodecane, to thereby obtain the intended compound. m.p. 140°–145° C.

EXAMPLE 9

Synthesis of 1,12-Bis(3,5-dihydroxyphenylcarboxy) dodecane

The same reaction as in Example 1 was carried out, except that 1,5-dibromopentane used in Synthesis Example 1 was replaced by the same mole of 1,12-dibromododecane, to thereby obtain the intended compound. m.p. 140°–145° C.

EXAMPLE 10

Synthesis of 1,4-Bis(3,5-dihydroxyphenylcarboxy) pentane

The same reaction as in Example 1 was carried out, except that 1,5-dibromopentane used in Synthesis Example 1 was replaced by the same mole of 1,4-dibromopentane, to thereby obtain the intended compound.

EXAMPLE 11

Synthesis of 1,5-Bis(3,5-dihydroxy-4-methylphenylcarboxy)pentane

The same reaction as in Example 1 was carried out, except that α-resorcylic acid used in Synthesis Example 1 was replaced by the same mole of 3,5-dihydroxy-4-methylbenzoic acid, to thereby obtain the intended compound. m.p. 205–°207° C.

EXAMPLE 12

Synthesis of 1,4-Bis[(3,5-dihydroxyphenylcarboxy) methyl]benzene

The same reaction as in Example 1 was carried out, except that 1,5-dibromopentane used in Synthesis Example 1 was replaced by the same mole of p-xylylene dibromide, to thereby obtain the intended compound. m.p. 220°–225° C.

EXAMPLE 13

Synthesis of 1,5-Bis(3,5-dihydroxyphenylcarboxy)-3-oxapentane

The same reaction as in Example 1 was carried out, except that 1,5-dibromopentane used in Synthesis Example 1 was replaced by the same mole of 1,5-bis(p-toluenesulfoxy)-3-oxapentane, to thereby obtain the intended compound. m.p. 190°–193° C.

EXAMPLE 14

Synthesis of 1,4-Bis(3,5-dihydroxyphenylcarboxy) butane-2-ene

The same reaction as in Example 1 was carried out, except that 1,5-dibromopentane used in Synthesis Example 1 was replaced by the same mole of 1,4-dichloro-2-butene, to thereby obtain the intended compound. m.p. 225°–230° C.

EXAMPLE 15

Synthesis of 1,4-Bis(3,5-dihydroxyphenylcarboxy) butane-2-ine

The same reaction as in Example 1 was carried out, except that 1,5-dibromopentane used in Synthesis Example 1 was replaced by the same mole of 1,4-dichloro-2-butine, to thereby obtain the intended compound. m.p. 230°–232° C.

EXAMPLE 16

Synthesis of 1,8-Bis(3,5-dihydroxyphenylcarboxy)- 3,6-dioxaoctane

The same reaction as in Example 1 was carried out, except that 1,5-dibromopentane used in Synthesis Example 1 was replaced by the same mole of 1,8-bis(p-toluenesulfoxy)-3, 5-dioxaoctane, to thereby obtain the intended compound. m.p. 166°–168° C.

EXAMPLE 17

Synthesis of 1,4-Bis[(3,5-dihydroxy-4-methylphenylcarboxy)methyl]benzene

The same reaction as in Example 1 was carried out, except that α-resorcylic acid and 1,5-dibromopentane used in Synthesis Example 1 were replaced by the same mole of 3,5-dihydroxy-4-methylbenzoic acid and p-xylylene dibromide respectively, to thereby obtain the intended compound. m.p. 276°–278° C.

EXAMPLE 18

Synthesis of 1,4-Bis[(3,5-dihydroxyphenylcarboxy) methyl]cyclohexane

The same reaction as in Example 1 was carried out, except that 1,5-dihydroxypentane used in Synthesis Example 2 was replaced by the same mole of 1,4-cyclohexane dimethanol, to thereby obtain the intended compound. m.p. 215°–220° C.

EXAMPLE 19

Synthesis of 1,4-Bis(3,5-dihydroxyphenylcarboxyethoxy)benzene

The same reaction as in Example 1 was carried out, except that 1,5-dibromopentane used in Synthesis Example 1 was replaced by the same mole of 1,4-bis(p-toluenesulfoxyethoxy)benzene, to thereby obtain the intended compound. m.p. 148°–152° C.

EXAMPLE 20

Synthesis of 4,4'-Bis(3,5-dihydroxyphenylcarboxyethoxyphenyl)sulfone

The same reaction as in Example 1 was carried out, except that 1,5-dibromopentane used in Synthesis Example 1 was replaced by the same mole of 4,4'-bis(p-toluenesulfoxyethoxyphenyl)sulfone, to thereby obtain the intended compound. m.p. 191°–193° C.

EXAMPLE 21

Synthesis of 2,2-Bis(3,5-dihydroxyphenylcarboxyethoxyphenyl)propane

The same reaction as in Example 1 was carried out, except that 1,5-dibromopentane used in Example 1 was replaced by the same mole of 2,2-bis(p-toluenesulfoxyethoxyphenyl) propane, to thereby obtain the intended compound. m.p. 50°–55° C.

EXAMPLE 22

Synthesis of 1,4-Bis(3,5-dihydroxyphenylcarboxyethoxycumyl)benzene

The same reaction as in Example 1 was carried out, except that 1,5-dibromopentane used in Synthesis Example 1 was replaced by the same mole of 1,4-bis(p-toluenesulfoxyethoxycumyl)benzene, to thereby obtain the intended compound. m.p. 95°–98° C.

EXAMPLE 23

Preparation of Recording Material (Preparation of Capsule Solution of Electron-Donating Dye Precursor)

In 20 parts of ethyl acetate was dissolved 3.0 parts of 3-(2-methyl-4-dimethylaminophenyl)-3-(1-ethyl-2-methylindole-3-yl)-4-azaphthalide (electron-donating dye precursor), and therewith was homogeneously admixed 20 parts of an alkylnaphthalene as a high boiling point solvent. To the mixture thus obtained, 20 parts of 3:1 adduct of xylylenediisocyanate and trimethylolpropane (in the form of 75 wt. % ethyl acetate solution) (Takenate D-110 N, trade name, a product of Takeda Chemical Industries, Ltd.) as a capsule wall material was added with stirring to make a homogeneous solution.

Separately, 54 parts of a 6% aqueous solution of polyvinyl alcohol (polymerization degree: 1,700; saponification degree: 88%) was prepared, and the electron-donating dye precursor described above was added thereto and then dispersed thereinto as an emulsion by means of a homogenizer. The emulsion thus obtained was admixed with 68 parts of water, followed by homogenization. The resulting emulsion was heated to 50° C. with stirring, and a capsulating reaction was carried out for 3 hours. Thus, the intended capsule solution was obtained. The capsules formed had an average particle diameter of 1.6 μm.

(Preparation of Dispersion of Electron-Accepting Compound)

30 parts of 1,5-bis(3,5-dihydroxyphenylcarboxy)pentane synthesized in Example 1 (electron-accepting compound) was added to 150 parts of a 4% water solution of polyvinyl alcohol, and dispersed thereinto for 24 hours by means of a ball mill, to thereby make a dispersion. The electron-accepting compound in the thus obtained dispersion had an average particle diameter of 1.2 μm. (Preparation of Coating Solution)

The foregoing capsule solution of the electron-donating dye precursor and the foregoing dispersion of the electron-accepting compound were mixed so that the molar ratio of the electron-donating dye precursor to the electron-accepting compound was 1/15, to thereby prepare the intended coating solution.

(Coating)

The coating solution prepared above as the solution for a heat-sensitive recording layer was applied to a 75 μm-thick polyethylene terephthalate support using a mayer bar and dried. Thus, the intended heat-sensitive recording material was obtained. The coverage of the electron-donating dye precursor was 0.3 g/m².

(Thermal Recording)

Printing on the foregoing heat-sensitive recording material was carried out using a thermal head, Model KST, made by Kyocera Co., Ltd. Therein, the potential applied to the thermal head and the pulse width thereof were determined so that the recording energy per unit area was 35 mJ/mm$^2$.

(Heat Resistance Evaluation of Color-Developed area)

The printed recording material was measured for density of the color developed therein by means of a Macbeth RD-918, and then stored in an 80° C. oven for 3 days. Thereafter, the printed part was measured again with a Macbeth RD-918. After measuring the color density, the remaining rate of the developed color density was determined using the following equation. Thus, the value thereof was found to be 78%.

Remaining rate of developed color density =

$$\frac{\text{(Density after storage for 3 days at 80° C.)}}{\text{(Density before storage)}} \times 100$$

A greater value of the remaining rate means that the developed color has a higher heat resistance.

EXAMPLE 24

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of bis(3,5-dihydroxyphenylcarboxy)methane. Therein, the remaining rate of the developed color density was found to be 97%.

EXAMPLE 25

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,2-bis(3,5-dihydroxyphenylcarboxy)ethane. Therein, the remaining rate of the developed color density was found to be 98%.

EXAMPLE 26

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,3-bis(3,5-dihydroxyphenylcarboxy)propane. Therein, the remaining rate of the developed color density was found to be 98%.

EXAMPLE 27

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,4-bis(3,5-dihydroxyphenylcarboxy)butane. Therein, the remaining rate of the developed color density was found to be 87%.

EXAMPLE 28

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,6-bis(3,5-dihydroxyphenylcarboxy)hexane. Therein, the remaining rate of the developed color density was found to be 85%.

EXAMPLE 29

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,5-bis(3,5-dihydroxy-4-methylphenylcarboxy)pentane. Therein, the remaining rate of the developed color density was found to be 86%.

EXAMPLE 30

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,4-bis[(3,5-dihydroxyphenylcarboxy)methyl]benzene. Therein, the remaining rate of the developed color density was found to be 92%.

EXAMPLE 31

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,5-bis(3,5-dihydroxyphenylcarboxy)-3-oxapentane. Therein, the remaining rate of the developed color density was found to be 78%.

EXAMPLE 32

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,4-bis(3,5-dihydroxyphenylcarboxy)butane-2-ene. Therein, the remaining rate of the developed color density was found to be 83%.

EXAMPLE 33

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 1,4-bis(3,5-dihydroxyphenylcarboxy)butane-2-ine. Therein, the remaining rate of the developed color density was found to be 95%.

COMPARATIVE EXAMPLE 1

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of bisphenol A. Therein, the remaining rate of the developed color density was found to be 61%.

COMPARATIVE EXAMPLE 2

The heat resistance evaluation of the color-developed area was made in the same manner as in Example 23, except that 1,5-bis(3,5-dihydroxyphenylcarboxy)pentane as the electron-accepting compound used in Example 23 was replaced by the same parts of 4-hydroxyphenyl-4'-isopropoxyphenylsulfone. Therein, the remaining rate of the developed color density was found to be 54%.

The present invention provides α-resorcylic acid ester derivatives which is effectively used as an electron-accepting compound, and recording materials containing these derivatives provided high heat resistance in the color-developed area thereof.

While the invention has been described in detail and with reference to specific examples thereof, it will be apparent to one skilled in the art that various changes and modifications can be made therein without departing from the spirit and scope thereof.

What is claimed is:

1. A recording material comprising a support having thereon a heat-sensitive recording layer comprising a binder, an electron-donating colorless dye and an electron-accepting compound, wherein said electron-accepting compound is an α-resorcylic acid ester derivative represented by the following general formula (I):

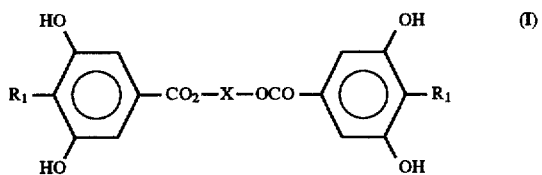

wherein $R_1$ represents a hydrogen atom, a halogen atom or an alkyl group; and X represents a divalent group selected from the group consisting of an alkylene group containing 1 to 20 carbon atoms, an aralkylene group containing 8 to 20 carbon atoms, an alkenylene group containing 4 to 18 carbon atoms, an alkynylene group containing 4 to 18 carbon atoms and an arylene group containing 6 to 12 carbon atoms.

2. A recording material as in claim 1, wherein $R_1$ is a hydrogen atom or alkyl group containing 1 to 4 atoms.

3. A recording material as in claim 2, wherein the alkylene group represented by X contains one of oxygen and sulfur atoms in its molecular chain.

4. A recording material as in claim 1, wherein the divalent group represented by X is an unsubstituted alkylene group containing 2 to 12 carbon atoms, an aralkylene group containing 8 to 12 carbon atoms, an unsubstituted alkenylene group containing 4 to 10 carbon atoms, or an alkylene group containing 5 to 12 carbon atoms and having an oxygen atom in its molecular chain.

5. A recording material as in claim 1, wherein the ratio of the electron-donating colorless dye to the α-resorcylic acid ester derivative in the recording layer is in the range from 1:10 to 1:1 by weight.

6. A recording material as in claim 1, wherein the recording layer comprises a heat-fusible material in a proportion ranging from 20 to 300% by weight to the α-resorcylic acid ester derivatives.

7. A recording material as in claim 4, wherein $R_1$ is a hydrogen atom or alkyl group containing 1 to 4 carbon atoms.

8. A recording material as in claim 4, wherein the ratio of the electron-donating colorless dye to the α-resorcylic acid ester derivative in the recording layer is in the range from 1:10 to 1:1 by weight.

9. A recording material as in claim 4, wherein the recording layer comprises a heat-fusible material in a proportion ranging from 20 to 300% by weight to the α-resorcylic acid ester derivatives.

* * * * *